United States Patent

Suzuki et al.

[11] Patent Number: 5,270,330
[45] Date of Patent: Dec. 14, 1993

[54] 2-NITROIMIDAZOLE DERIVATIVE, PRODUCTION THEREOF, AND RADIOSENSITIZER CONTAINING THE SAME AS ACTIVE INGREDIENT

[75] Inventors: Toshimitsu Suzuki; Masakazu Sakaguchi; Yoshiyuki Miyata; Akira Suzuki; Tomoyuki Mori, all of Yokohama, Japan

[73] Assignee: Pola Chemical Industries, Inc., Shizuoka, Japan

[21] Appl. No.: 915,814
[22] PCT Filed: Jan. 24, 1991
[86] PCT No.: PCT/JP91/00074
§ 371 Date: Jul. 24, 1992
§ 102(e) Date: Jul. 24, 1992
[87] PCT Pub. No.: WO91/11440
PCT Pub. Date: Aug. 8, 1991

[30] Foreign Application Priority Data

Jan. 26, 1990 [JP] Japan .................. 2-16721

[51] Int. Cl.⁵ ............... A61K 31/415; C07D 233/91
[52] U.S. Cl. .................. 514/398; 548/327.5
[58] Field of Search .......... 548/327.5; 514/398

[56] References Cited

U.S. PATENT DOCUMENTS 4,462,992  7/1984  Agrawal et al. ............ 548/327.5
4,945,102  7/1990  Suzuki et al. ............. 548/327.5

FOREIGN PATENT DOCUMENTS 59-139363  8/1984  Japan ................. 548/327.5
60-75430   4/1985  Japan .
1-110675   4/1989  Japan .

*Primary Examiner*—Mary C. Lee
*Assistant Examiner*—Fiona T. Powers
*Attorney, Agent, or Firm*—Bacon & Thomas

[57] ABSTRACT

The present invention relates to a 2-nitroimidazole derivative represented by the following general formula (I):

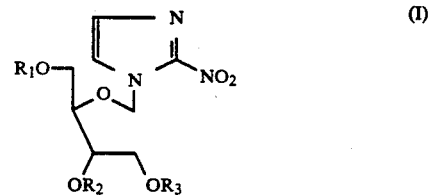

wherein $R_1$, $R_2$ and $R_3$ may be the same or different from each other and mean individually a hydrogen atom or an acyl group, and a radiosensitizer containing the same. The compound (I) according to this invention has an excellent radiosensitizing effect and high safety, so that a radiosensitizer containing the same is remarkably useful in the radiotherapy of cancers.

2 Claims, No Drawings

2-NITROIMIDAZOLE DERIVATIVE, PRODUCTION THEREOF, AND RADIOSENSITIZER CONTAINING THE SAME AS ACTIVE INGREDIENT

TECHNICAL FIELD

This invention relates to a 2-nitroimidazole derivative, which is a novel substance useful as a radiosensitizer for hypoxic cells, a production process thereof, and a radiosensitizer containing the same as an active ingredient.

BACKGROUND ART

Cancers are difficult to cure even at the present day, and hence inflict great pains and economical losses on the world. Broadly speaking, a cancer is treated by three therapies of radiotherapy, chemotherapy and surgical therapy.

In the radiotherapy for the cancer among these, the presence of hypoxic cells in the tumor becomes the greatest problem. The hypoxic cells have high resistance to radioactive rays and are hence believed to be a serious cause of the refractoriness and/or the recurrence in the radiotherapy. On the other hand, no hypoxic cells exist in any normal tissues. Upon performing the radiotherapy for the cancer, it is therefore important to enhance the radiosensitivity of the hypoxic cells in the tumor.

In view of the foregoing circumstances, the present inventors carried out an extensive investigation with a view toward providing a medicament by which the radiosensitivity of normal cells is unchanged and only hypoxic cells are sensitized when radiotherapy is performed, i.e., a radiosensitizer for hypoxic cells (hereinafter referred to as "radiosensitizer"). As a result, it has been found that a 2-nitroimidazole derivative represented by the general formula (I) which will be described subsequently has a high radiosensitizing effect even in a low concentration and is also low in toxicity which has heretofore become the greatest problem, leading to completion of the present invention.

DISCLOSURE OF THE INVENTION

The present invention provides a 2-nitroimidazole derivative represented by the following general formula (I):

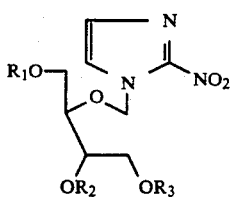

wherein $R_1$, $R_2$ and $R_3$ may be the same or different from each other and mean individually a hydrogen atom or an acyl group, and a production process thereof. The present invention further provides a radiosensitizer containing this derivative as an active ingredient.

BEST MODE FOR CARRYING OUT THE INVENTION

In the general formula (I) by which the compound according to this invention is represented, examples of the acyl groups indicated by $R_1$, $R_2$ and $R_3$ include alkanoyl, alkenoyl or aroyl groups having 1–10 carbon atoms. The illustrative representatives of the compounds (1) according to this invention are as follows:

(1) 1-[(2′,3′-diacetoxy-1′-acetoxymethyl)propoxy]methyl-2-nitroimidazole;
(2) 1-[(2′,3′-dipropionoxy-1′-propionoxymethyl)propoxy]methyl-2-nitroimidazole;
(3) 1-[(2′,3′-diacryloxy-1′-acryloxymethyl)propoxy]methyl-2-nitroimidazole;
(4) 1-[(2′,3′-dicrotonoxy-1′-crotonoxymethyl)propoxy]methyl-2-nitroimidazole;
(5) 1-[(2′,3′-dibenzoxy-1′-benzoxymethyl)propoxy]methyl-2-nitroimidazole; and
(6) 1-[(2′,3′-dihydroxy-1′-hydroxymethyl)propoxy]methyl-2-nitroimidazole.

The compound (I) of this invention can be produced in accordance with, for example, the following reaction formula:

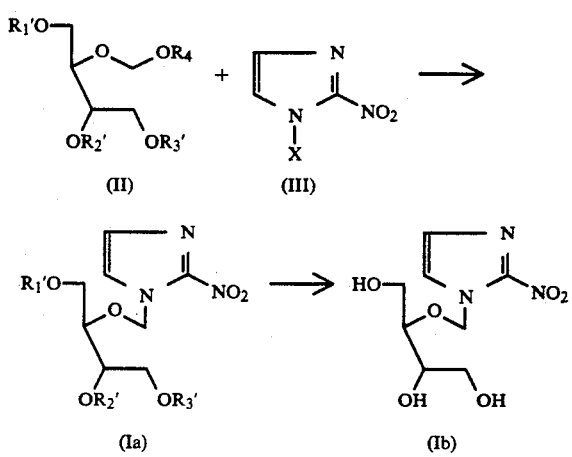

wherein $R_1'$, $R_2'$ and $R_3'$ may be the same or different from each other and mean individually an acyl group, $R_4$ denotes an acyl group, and X stands for a hydrogen atom or a trialkylsilyl group.

Namely, 1,2,4-triacyloxy-3-acyloxymethoxybutane (II) is reacted with 2-nitroimidazole or a trialkylsilyl-containing product thereof (III), thereby producing a compound (Ia) in which $R_1$, $R_2$ and $R_3$ in the formula (I) are individually an acyl group. Further, the hydrolysis of the compound (Ia) produces a compound (Ib) in which $R_1$, $R_2$ and $R_3$ in the formula (I) are individually a hydrogen atom.

In the above-described reaction formula, the reaction in the case where the compound (III) is 2-nitroimidazole is preferably carried out by melting the compound (II) and 2-nitroimidazole in the presence of a catalyst while reducing pressure. Various kinds of catalysts may be used as such a catalyst. For example, proton acids such as paratoluenesulfonic acid, methanesulfonic acid and trichloroacetic acid, and Lewis acids such as anhydrous zinc chloride, anhydrous aluminum chloride and anhydrous stannic chloride may be used. Among these, paratoluenesulfonic acid is the most effective catalyst owing to formation of little by-product. The proportions of the compound (II) and 2-nitroimidazole to be used may be optionally determined. However, it is generally desirable that the former compound should be used in a range of from an amount equimolar to the latter compound to an amount slightly in excess of the same. In general, the reaction is preferably conducted at a temperature of 50°-150° C. The reaction time may vary according to the reaction reagents, solvent, temperature, reaction-accelerating substance, etc. to be used, but is generally 30 minutes to 6 hours.

On the other hand, the reaction in the case where the compound (III) is 1-trialkylsilyl-2-nitroimidazole is preferably carried out by reacting the compound (II) with 1-trialkylsilyl-2-nitroimidazole in the presence of a Lewis acid.

1-Trialkylsilyl-2-nitroimidazole which is a raw compound can be obtained as a raw material usable as it is by reacting 2-nitroimidazole with N,O-bistrialkyl-silylacetamide in an excess amount while stirring them at room temperature or under heat and then distilling under reduced pressure the unreacted silylating agent out of the reaction mixture.

Various kinds of acids may be used as the Lewis acid. As exemplary Lewis acids, may be mentioned anhydrous stannic chloride, anhydrous aluminum chloride, anhydrous zinc chloride and the like. These acids may preferably be used in a catalytic amount or an amount equivalent to the compound (II). The proportions of the compound (II) and 1-trialkylsilyl-2-nitroimidazole to be used may be optionally determined. However, it is generally preferred that the compound (II) should be used in a range of from an amount equimolar to 1-trialkylsilyl-2-nitroimidazole to an amount slightly in excess of the same. Various kinds of solvents may be used as a solvent for the reaction. For example, acetonitrile, methylene chloride, benzene, toluene and the like are however preferred. The reaction may be performed at a temperature ranging from −30° to 50° C. However, it is generally preferred to conduct the reaction under water cooling or at room temperature. The reaction time may vary according to the reaction reagents, temperature, reaction solvent, catalyst, etc. to be used. However, it is generally preferred to conduct the reaction for 30 minutes to 6 hours.

After completion of the reaction according to any one of the above-described two processes, the intended product is separated from the reaction mixture and purified by a method known per se in the art. For example, the reaction mixture is subjected to extraction, and the extract is washed with water, concentrated and then purified by preparative thin-layer chromatography, column chromatography or the like, thereby obtaining a compound (Ia) with high yield.

The hydrolysis reaction of the compound (Ia) is conducted by a method in which the compound (Ia) is treated overnight under ice cooling or at room temperature in an absolute alcohol containing sodium alcoholate therein or an absolute alcohol with ammonia gas saturated therein, a method in which the compound (Ia) is hydrolyzed with an organic base such as triethylamine or pyridine in a water-containing alcohol at a temperature ranging from room temperature to 80° C., or the like. Examples of the alcohol used include lower alcohols such as methyl alcohol, ethyl alcohol and propyl alcohol.

The compound (I) of this invention is low in toxicity as demonstrated by Test Example which will be described subsequently, and has an excellent radiosensitizing effect. The compound (I) of this invention is preferably administered 15 minutes through 5 hours prior to the irradiation of radioactive rays. The administration is carried out orally or parenterally. The compound (I) may be prepared in the form of tablets, capsules, granules, powder, suppository or injection by suitably adding additives such as an excipient, stabilizer, preservative and buffer. The dose the compound (I) may vary according to age, the site of tumorigenesis, the kind of tumor, symptoms and the like. However, it is generally preferable to dose the compound (I) in an amount of 0.2 g through 5.0 g/m$^2$ of area of body surface.

The acute toxicity test and radiosensitizing effect of the compound (I) according to this invention will hereinafter be described by the following test examples.

(1) Acute toxicity test

Using ICR male mice after the elapse of 5 weeks from their birth, 1-[(2′,3′-dihydroxy-1′-hydroxy)propoxy]-methyl-2-nitroimidazole [the representative compound (6)] dissolved in physiological saline was intravenously administered to them. The mice were observed over 14 days after the administration to determine the 50% lethal dose ($LD_{50/14}$). As a result, it was found to be 5,900 mg/kg.

(2) Test of radiosensitizing effect

1) In vitro test 1

Cell used: Single cells of BMT-6
Radioactive ray irradiated: $^{60}Co$ - γ rays
Oxygen-reducing treatment: A mixed gas composed of 95% nitrogen and 5% carbon dioxide gas is caused to flow into a cell suspension.
Judgment of survival rate of the cells: According to a colony counting method Radiosensitization ratio (Enhancement Ratio = ER):

$$ER = \frac{\text{Dose required to attain a certain biological effect in a group administered with no compound}}{\text{Dose required to attain the same biological effect as that in the group administered with no compound in a group administered with the compound}}$$

The result obtained under the above-described conditions is as follows:

ER of the representative compound (6) in a concentration of 1 mM: 1.67

2) In vivo test

Animal used: Balb/c mice
Tumor used: BMT-6
Substance tested: Representative compound (6) 200 mg/kg
Dosing manner: Intravenous administration of the representative compound (6) dissolved in physiological saline 15 minutes prior to the irradiation of radioactive rays
Radioactive ray irradiated: $^{60}Co$ - γ rays, the whole body irradiation
Judgment of radiosensitizing effect: A radiosensitization ratio (ER) was determined from the dose and the reduction percent of tumor cells to conduct the judgment of the effect.

The result obtained under the above-described conditions is as follows:

ER of the representative compound (6) in a dose of 200 mg/kg: 1.44

EXAMPLES

The present invention will hereinafter be described in more detail by the following Reference Example and Examples. However, it should be borne in mind that this invention is not limited to and by these examples.

REFERENCE EXAMPLE 1

Synthesis of 1,3,4-triacetoxy-2-acetoxymethoxy-butane (1) Fifty grams of meso-erythritol were dispersed in 700 ml of pyridine. To the resulting dispersion, 3 equivalent weights (125.3 g) of acetic anhydride were added dropwise under water cooling so as to gradually form a transparent solution. Most of pyridine was then distilled out of the solution by a rotary evaporator. The residue was added with 500 ml of ethyl acetate, thereby subjecting it to extraction. The extract was then washed with water. Thereafter, the ethyl acetate layer was dried by anhydrous sodium sulfate and then concentrated. The concentrate was subjected to column chromatography on silica gel. First of all, elution was carried out with benzene, thereby obtaining tetraacetoxy-meso-erythritol. Then, 26 g of 1,3,4-triacetoxy-meso-erythritol was eluted with a 9:1 mixed solvent of benzene and ethyl acetate.

(2) To 26 g of 1,3,4-triacetoxy-meso-erythritol thus obtained, 200 ml of dimethoxyethane was added to mix them into a solution. Phosphorus pentoxide was added to the resultant solution while stirring it under water cooling. At this time, the addition was conducted while checking by TLC (developing solution: benzene:ethyl acetate=1:1). The addition of phosphorus pentoxide was stopped at the time when a TLC became one spot, thereby completing the reaction. A supernatant liquid of the reaction mixture was shifted to a separatory funnel, thereby subjecting it to extraction with 200 ml of n-hexane. The extract was then added with an aqueous saturated solution of sodium bicarbonate. The resulting mixture was washed with water and dried by anhydrous sodium sulfate. The solvent was then distilled out of the mixture, thereby obtaining 30.5 g of 1,3,4-triacetoxy-2-methoxymethoxy-butane.

(3) To 30.5 g of 1,3,4-triacetoxy-2-methoxymethoxybutane obtained in the step (2), 15 g of acetic anhydride was added to mix them. The resultant mixture was cooled with ice. After thoroughly cooled with ice, 4 ml of boron trifluoride etherate was added dropwise to react them for 1 hour with stirring. After completion of the reaction, the reaction mixture was poured into iced water mixed with a great excess of sodium bicarbonate, thereby decomposing unreacted acetic anhydride to neutralize the reaction mixture. Thereafter, 200 ml of ethyl acetate was added, thereby subjecting the reaction mixture to extraction. The extract was washed with water and dried (by sodium sulfate), thereby obtaining 30.0 g of 1,3,4-triacetoxy-2-acetoxymethoxy-butane.

EXAMPLE 1

Synthesis of 1-[(2',3'-diacetoxy-1'-acetoxymethyl)propoxy]methyl-2-nitroimidazole A flask was charged with 5.6 g of 2-nitroimidazole, 16.0 g of 1,3,4-triacetoxy-2-acetoxymethoxybutane and 0.5 g of p-toluenesulfonic acid monohydrate. A trap was attached to the flask to connect it to aspirator so as to permit the reduction of the pressure within the flask. The flask was immersed in an oil bath of 130°-140° C. while reducing the pressure within the flask and stirring the contents. Acetic acid distilled off as a reaction advanced. The reaction was completed in about 15 minutes. After the reaction mixture was cooled to room temperature, about 300 ml of ethyl acetate was added to the reaction mixture, thereby subjecting it to extraction. The extract was washed with an aqueous saturated solution of sodium hydrogencarbonate and then with water. The thus-washed extract was dried by anhydrous sodium sulfate and then concentrated under reduced pressure. The residue was purified by preparative high speed liquid chromatography on a silica gel column making use of a mixed solvent of ethyl acetate-benzene as an eluting solution, thereby obtaining the title compound (15.3 g, yield: 52%) as a viscous oil.

MS (m/e): 373 (M+)

IR (cm$^{-1}$): 1740(CO), 1535(NO$_2$), 1490(NO$_2$)

NMR ($\delta$, CDCl$_3$) 2.0(s,9H,CH$_3$COx3), 3.6–4.4(m,5-H,—CH$_2$OAcx2, =CH—), 5.1(m,1H,=CH—OAc), 7.1 (s,1H,ring proton), 7.3(s,1H,ring proton)

EXAMPLE 2

Synthesis of 1-[(2',3'-dihydroxy-1'-hydroxymethyl)propoxy]methyl-2-nitroimidazole In 50 ml of absolute methanol, 3.73 g of 1-[(2',3'-diacetoxy-1'-acetoxymethyl)propoxy]methyl-2-nitroimidazole was dissolved. While stirring the resulting solution at room temperature, a 5% solution of sodium ethoxide in absolute ethanol was added dropwise until the pH of the solution turned to 9.0. After stirring the resulting reaction mixture for 3 hours at room temperature, "Dowex 50W" (H+, product of Dow Chemical Co.) was slowly added until the pH of the reaction mixture turned to 7.0. After Dowex 50W was then removed by filtration under reduced pressure, the solvent was distilled off under reduced pressure, and the residue was recrystallized from ethanol, thereby obtaining 1.48 g (yield: 60%) of the title compound as pale yellow needle crystals.

MS (m/e): 248 (M+)

IR (cm$^{-1}$): 3450(OH), 1540(NO$_2$), 1490(NO$_2$)

NMR [$\delta$, DMSO(d$_6$)]: 3.2–3.6(m,7H,=CH—OH-,—CH$_2$OHx2, =CH—), 4.1–4.6(m,3H,OHx3), 5.8(s,2H,—OCH$_2$N=), 7.1 (s,1H,ring proton), 7.7(s,1H,ring proton)

EXAMPLE 3

Synthesis of 1-[(2,3-diacetoxy-1-acetoxymethyl)propoxy]methyl-2-nitroimidazole

A flask equipped with a calcium chloride cylinder was charged with 5.6 g of 2-nitroimidazole and 30 ml of N,O-bistrimethylsilylacetamide (BSA). The contents were stirred at 40°–50° C. to gradually form a transparent solution. One through two hours later, 2-nitroimidazole was completely converted into a silyl-containing compound. Unreacted BSA and O-trimethylsilylacetamide as a by-product were distilled off under reduced pressure at a temperature of 90° C. or higher to use them in the next reaction as they are. The thus-obtained silyl-containing 2-nitroimidazole was added with 16.0 g of 1,3,4-triacetoxy-2-acetoxymethoxybutane and 20 ml of anhydrous acetonitrile. Then, 10 ml of anhydrous stannic chloride was added dropwise under water cooling. The contents were stirred for 2–3 hours to react them. The reaction mixture was poured.

into 500 ml of ethyl acetate containing 100 g of ice therein. The mixture was stirred while further adding anhydrous sodium hydrogencarbonate until bubbles of carbon dioxide became free from generation. After the ethyl acetate layer was washed with water and dried by anhydrous sodium sulfate, the solvent was distilled off under reduced pressure. The residue was purified by preparative high speed liquid chromatography on a silica gel column making use of a mixed solvent of ethyl acetatebenzene as an eluting solution, thereby obtaining the title compound (15.1 g, yield: 81%).

EXAMPLE 4

Synthesis of 1-[(2',3'-dihydroxy-1'-hydroxymethyl)propoxy]methyl-2-nitroimidazole In 100 ml of methanol containing 10% of water, 3.73 g of 1-[(2',3'-diacetoxy-1'-acetoxymethyl)propoxy]methyl-2-nitroimidazole was dissolved. To the resulting solution, 10 g of triethylamine was added to react them for 4 hours at room temperature with stirring. After completion of the reaction, the solvent was distilled off by an evaporator, and the residue was recrystallized from ethanol, thereby obtaining the title compound as colorless needle crystals with a yield of 57%.

INDUSTRIAL APPLICABILITY

The compound (I) according to this invention has an excellent radiosensitizing effect and high safety, so that a radiosensitizer containing the compound (I) is remarkably useful in the radiotherapy of cancers.

We claim:

1. A 2-nitroimidazole derivative represented by the following general formula (I):

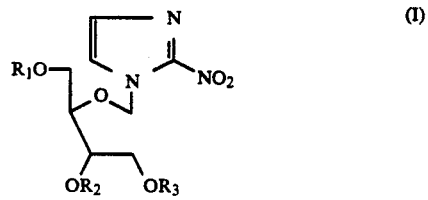

wherein $R_1$, $R_2$ and $R_3$ may be the same or different from each other and mean individually a hydrogen atom or an acyl group.

2. A radiosensitizer containing, as an active ingredient, the 2-nitroimidazole derivative as set forth in claim 1 and an additive.

* * * * *